United States Patent
Kim

(10) Patent No.: US 10,702,564 B2
(45) Date of Patent: Jul. 7, 2020

(54) **BLOOD PRESSURE LOWERING COMPOSITION CONTAINING AS ACTIVE INGREDIENT EXOPOLYSACCHARIDE PRODUCED BY MEANS OF *CERIPORIA LACERATA***

(71) Applicant: FUGENBIOPHARMA CO., LTD., Seoul (KR)

(72) Inventor: Yoon Soo Kim, Seongnam-si (KR)

(73) Assignee: FUGENBIOPHARMA CO., LTD., Seoul (KR)

( * ) Notice: Subject to any disclaimer, the term of this patent is extended or adjusted under 35 U.S.C. 154(b) by 134 days.

(21) Appl. No.: 15/523,710

(22) PCT Filed: Nov. 3, 2015

(86) PCT No.: PCT/KR2015/011698
§ 371 (c)(1),
(2) Date: May 2, 2017

(87) PCT Pub. No.: WO2016/072697
PCT Pub. Date: May 12, 2016

(65) Prior Publication Data
US 2017/0360860 A1 Dec. 21, 2017

(30) Foreign Application Priority Data
Nov. 3, 2014 (KR) .................. 10-2014-0151598

(51) Int. Cl.
| | | |
|---|---|---|
| *A01N 65/00* | (2009.01) | |
| *A61K 36/06* | (2006.01) | |
| *A61K 36/09* | (2006.01) | |
| *A01N 63/04* | (2006.01) | |
| *A61K 39/00* | (2006.01) | |
| *A61K 39/38* | (2006.01) | |
| *A61K 36/07* | (2006.01) | |
| *A23L 33/10* | (2016.01) | |

(52) U.S. Cl.
CPC .............. *A61K 36/07* (2013.01); *A23L 33/10* (2016.08); *A61K 36/06* (2013.01); *A23V 2002/00* (2013.01); *A61K 2236/00* (2013.01); *A61K 2236/11* (2013.01); *A61K 2236/17* (2013.01); *A61K 2236/30* (2013.01)

(58) Field of Classification Search
CPC ........ A61K 36/07; A61K 36/06; A61K 38/00; A61K 39/0002
See application file for complete search history.

(56) References Cited

U.S. PATENT DOCUMENTS

2014/0193454 A1* 7/2014 Kim .................. A61K 36/07
424/195.15

FOREIGN PATENT DOCUMENTS

| WO | 2014/112666 A1 | 7/2014 |
|---|---|---|
| WO | WO 2014/112666 A1 * | 7/2014 |
| WO | 2016010183 A1 | 1/2016 |

OTHER PUBLICATIONS

Henda et al., J. Agric. Food Chem., 2013; 61: 10685-10690.*
Maruyama et al., Agric. Biol. Chem., V51 (9), 2557-2561, 1987.*
Iwaniak et al., Comprehensive Reviews Food Science & Safety, vol. 13, 114-134, 2014.*
German Patent Office; Communication dated Aug. 7, 2018 in counterpart application No. 112015004985.1, Not translated.
R.A. Defronzo, "Insulin resistance: a multifaceted syndrome responsible for NIDDM, obesity, hypertension, dyslipidaemia and atherosclerosis", The Netherlands Journal of Medicine, 1997, pp. 119-197, vol. 50 (7 pages total).
Ji-Eun Kim et al., "Hyperglycemic Effect of Submerged Culture Extract of Ceriporia lacerata in Streptozotocin-induced Diabetic Rats", Food Sci. Biotechnol., 2012, pp. 1685-1693, vol. 21, No. 6.
Korean Patent Office, Office Action for corresponding Korean Application No. 10-2014-0151598, dated May 23, 2016.
International Searching Authority, International Search Report for PCT/KR2015/011698, dated Feb. 15, 2016.

* cited by examiner

*Primary Examiner* — Gary B Nickol
*Assistant Examiner* — Lakia J Jackson-Tongue
(74) *Attorney, Agent, or Firm* — Sughrue Mion, PLLC

(57) ABSTRACT

The present invention relates to a blood pressure lowering composition which contains as an active ingredient exopolysaccharide produced by means of *Ceriporia lacerata*, a *Ceriporia lacerata* mycelium culture medium comprising same, or dry powder or an extract of same. The composition can be used as an antihypertensive for preventing or treating hypertension or cerebral apoplexy or as a functional health food having antihypertensive effect.

13 Claims, 1 Drawing Sheet

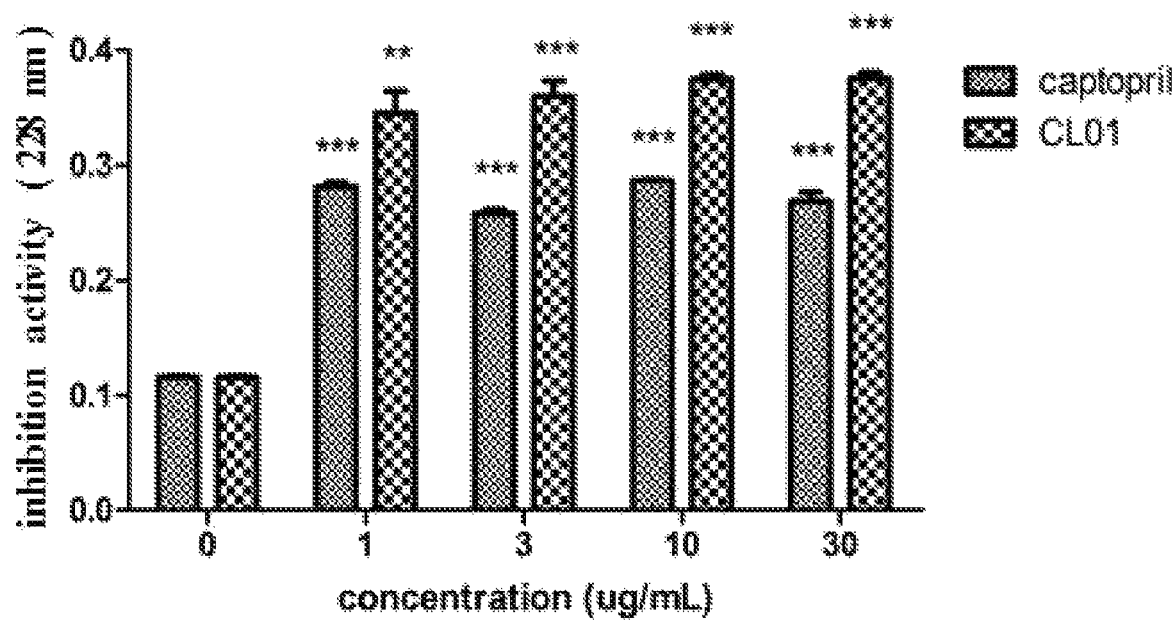

BLOOD PRESSURE LOWERING
COMPOSITION CONTAINING AS ACTIVE
INGREDIENT EXOPOLYSACCHARIDE
PRODUCED BY MEANS OF *CERIPORIA
LACERATA*

CROSS REFERENCE TO RELATED
APPLICATIONS

This is a National Stage of Application No. PCT/KR2015/011698 filed Nov. 3, 2015, claiming priority based on Korean Patent Application No. 10-2014-0151598 filed Nov. 3, 2014, the contents of all of which are incorporated herein by reference in their entirety.

TECHNICAL FIELD

The present invention relates to a composition for lowering blood pressure, comprising an extracellular polysaccharide produced by *Ceriporia lacerata*, a mycelial culture medium of *Ceriporia lacerata* containing the same, or dried powders or an extract thereof, as an effective ingredient.

BACKGROUND ART

In recent years, the number of people suffering from lifestyle-derived diseases such as hypertension is increasing rapidly due to western style diet and lifestyle pattern changes. The incidence of hypertension is gradually increasing worldwide.

It is known that the main causes of hypertension are increased peripheral vascular resistance, the action of endothelin (ET), the increase of free oxygen radicals and the action of nitric oxide, the contraction of blood vessels due to insulin resistance, and the renin-angiotensin system disturbance, etc. Among them, the renin-angiotensin system has been actively investigated recently. If the blood pressure gets low, renin converts angiotensinogen to angiotensin I, and angiotensin converting enzyme (ACE) converts angiotensin I into angiotensin II, an active hormone, thereby increasing blood pressure, activating sympathetic nerves and maintaining electrolyte balance. More specifically, the angiotensin converting enzyme (ACE) is an enzyme playing a role in converting angiotensin I, a decapeptide, to angiotensin II, a vasoconstrictor, by cutting dipeptide (His-Leu) from angiotensin I. a decapeptide. The increase of angiotensin II promotes strong blood pressure elevation action and secretion of aldosterone, an antidiuretic hormone, which inhibits the excretion of water and sodium and thus increases circulating blood volume, thereby inducing hypertension. In addition, ACE decomposes and inactivates bradykinin, a vascular relaxant, resulting in the elevation of blood pressure. Therefore, the ACE inhibitor has provided a breakthrough in the treatment of hypertension, which prevents vasoconstriction by inhibiting the action of ACE, thereby showing blood pressure-lowering effect. As a representative ACE inhibitor, captopril, a chemically synthesized agent, has been developed and used as a therapeutic agent for hypertension. However, it shows many adverse events such as dry cough, headache, loss of appetite, taste dysfunction, rash, decrease of leukocytes, etc., and thus, recent researches have been focused on the development of ACE inhibitors from a natural product which does not show adverse event. Although ACE inhibiting peptides derived from the plasma of slaughtered blood, as natural products, have been reported in Korea (Korean Patent No. 0215090 and Korean Patent No. 0215091), the research on ACE inhibiting substance from *Ceriporia lacerata* has not been known.

*Ceriporia lacerata* is a kind of white-rotting fungus and known to conduct co-metabolism, i.e., lignin decomposition, in order to use carbon sources such as cellulose, hemicellulose, other polysaccharides, and glycerol, etc., in the ecosystem. However, since *Ceriporia lacerata* was first reported to academic world in 2002, the research on the industrialization of *Ceriporia lacerata* has not been done sufficiently.

Accordingly, the present inventors have found that an extracellular polysaccharide produced by *Ceriporia lacerata*, a mycelial culture medium of *Ceriporia lacerata* containing the same, or dried powders or an extract thereof shows a blood pressure-lowering effect, and have completed the present invention which is related to a composition for lowering blood pressure, comprising the extracellular polysaccharide, the mycelial culture medium, the dried powders, or the extract, as an effective ingredient.

DISCLOSURE OF INVENTION

Technical Problem

It is an object of the present invention to provide a composition for lowering blood pressure, comprising a pharmacologically active ingredient produced by *Ceriporia lacerata*.

It is another object of the present invention to provide a health functional food having blood pressure-lowering effect, comprising a pharmacologically active ingredient produced by *Ceriporia lacerata*.

Solution to Problem

In accordance with one object of the present invention, there is provided a composition for lowering blood pressure, comprising an extracellular polysaccharide produced by *Ceriporia lacerata*; a mycelial culture medium of *Ceriporia lacerata* containing the extracellular polysaccharide; dried powders of the mycelial culture medium; or an extract of the mycelial culture medium, as an effective ingredient.

In accordance with another object of the present invention, there is provided a health functional food having blood pressure-lowering effect, comprising an extracellular polysaccharide produced by *Ceriporia lacerata*; a mycelial culture medium of *Ceriporia lacerata* containing the extracellular polysaccharide; dried powders of the mycelial culture medium; or an extract of the mycelial culture medium, as an effective ingredient.

In accordance with another object of the present invention, there is provided a method for lowering blood pressure comprising administering to a subject in need of lowering blood pressure an extracellular polysaccharide produced by *Ceriporia lacerata*; a mycelial culture medium of *Ceriporia lacerata* containing the extracellular polysaccharide; dried powders of the mycelial culture medium; or an extract of the mycelial culture medium.

In accordance with another object of the present invention, there is provided a use of an extracellular polysaccharide produced by *Ceriporia lacerata*; a mycelial culture medium of *Ceriporia lacerata* containing the extracellular polysaccharide; dried powders of the mycelial culture medium; or an extract of the mycelial culture medium for preparing a drug for lowering blood pressure.

Advantageous Effects of Invention

A composition comprising an extracellular polysaccharide produced by *Ceriporia lacerata*, a mycelial culture medium of *Ceriporia lacerata* containing the same, or dried powders or an extract thereof, as an effective ingredient, shows an excellent ACE inhibition activity, and thus can be usefully employed for lowering blood pressure.

BRIEF DESCRIPTION OF DRAWINGS

FIG. 1 is a graph comparing ACE inhibition activities of captopril and an extracellular polysaccharide produced by *Ceriporia lacerata*.

BEST MODE FOR CARRYING OUT THE INVENTION

Hereinafter, the present invention is explained in detail.

In the present invention, there is provided a composition for lowering blood pressure, which contains an extracellular polysaccharide produced by *Ceriporia lacerata*; a mycelial culture medium of *Ceriporia lacerata* containing the extracellular polysaccharide; or dried powders or an extract thereof, as an effective ingredient.

In a composition according to the present invention, the extracellular polysaccharide may comprise about 40 to 60 wt % of sugar and about 30 to 40 wt % of protein, about 40 to 50 wt % of sugar and about 32 to 38 wt % of protein, or about 43 to 47 wt % of sugar and about 33 to 36 wt % of protein, preferably about 45 wt % of sugar and about 34 wt % of protein.

The sugar may include mannose, galactose and glucose.

The extracellular polysaccharide may have a molecular weight of about 100 to 150 kDa, about 110 to 140 kDa or about 115 to 125 kDa, preferably about 120 kDa.

According to one preferred embodiment of the present invention, the extracellular polysaccharide may be prepared by a preparation method comprising the steps of: (a) culturing mycelia of *Ceriporia lacerata* in a liquid to prepare a mycelial culture medium of *Ceriporia lacerata*, (b) drying the mycelial culture medium of *Ceriporia lacerata* to form powders, and (c) extracting the powders of the mycelial culture medium of *Ceriporia lacerata* with a solvent, and filtering and concentrating the resultant extract under reduced pressure.

The medium for culturing in a liquid in step (a) may contain sugar, glucose, starch, sorghum powder, barley powder, soybean flour, magnesium sulfate ($MgSO_4$), monopotassium phosphate ($KH_2PO_4$), dipotassium phosphate ($K_2HPO_4$) and water, and the hydrogen ion concentration (pH) of the medium may be 4.5 to 6.0.

According to one preferred embodiment of the present invention, the medium may contain 0.2 to 3 wt % of sugar, 0.2 to 3 wt % of glucose, 0.2 to 4 wt % of starch, 0.1 to 0.5 wt % of sorghum powder, 0.1 to 0.5 wt % of barley powder, 0.2 to 3 wt % of soybean flour, 0.05 to 0.1 wt % of magnesium sulfate (MgSO4), 0.05 to 0.25 wt % of monopotassium phosphate ($KH_2PO_4$), 0.05 to 0.25 wt % of dipotassium phosphate ($K_2HPO_4$) and residual quantity of water.

The culture in a liquid of step (a) may be conducted under a blue LED light source, and may be conducted with a carbon dioxide concentration maintained at 1,000 to 2,000 ppm.

For example, the culture in a liquid may be conducted for 8 to 13 days at 20 to 25° C., under a blue LED light source, with the pH maintained at 4.5 to 6.0, an illuminance maintained at 0.5 LUX, an air injected at 0.5 to 1.5 $kgf/cm^2$, and carbon dioxide concentration maintained at 1,000 to 2,000 ppm, and preferably, the culture is conducted for 10 days under the condition of 22° C., pH 5.0, 1.0 $kgf/cm^2$, and 1,500 ppm, to obtain a high content of an extracellular polysaccharide.

The parent strain for use in step (a) may be a strain obtained by culturing a dominant strain stored in PDA (Potato dextrose agar) medium at 4° C. in PDB (Potato dextrose broth) medium in Erlenmeyer flask using a shaking incubator at a constant temperature of 25° C. for 7 to 9 days. Herein, the amount of the mycelium to be inoculated is preferably about 0.5% (w/v) based on the solution to be cultured. Since a high amount of the mycelia (%/100 mL) does not necessarily result in a high content of the extracellular polysaccharide, the medium composition may be preferably selected such that it provides a condition for maximizing the content of extracellular polysaccharide, rather than the best condition for the growth of mycelia.

The culture medium may be separated and purified into mycelia and an aqueous solution. For the separation and purification, the mycelia may be removed from the culture medium using a centrifuge and the remaining solution may be repeatedly purified using a Multi-Sheet Filter Press and a vibrating membrane separator (PALLSEP), followed by irradiation with UV rays for 1 minute. Also, the solution needs to be sealed and stored after removing oxygen, since the presence of mycelia in the solution results in the change in the content of the effective ingredient due to the growth of the mycelia.

In step (b), the mycelial culture medium prepared in step (a) may be vacuum dried or freeze dried to form powders. In order to prevent the loss of an effective substance, the drying is preferably carried out at a temperature of 40° C. or lower, preferably 30° C. or lower, for 48 to 96 hours. In addition, for the drying in step (b), a vacuum freeze dryer is preferably used rather than a vacuum dryer in which a relatively high evaporation temperature is set, in terms of minimizing the change in the content of the effective substance.

In step (c), the dried powders of a mycelial culture medium obtained in step (b) are extracted with a solvent, an extracellular polysaccharide, an effective ingredient according to the present invention, is isolated and prepared.

Specifically, 100 mL of distilled water may be added to 5 g of dried powders, and the resultant suspension may be centrifuged (8,000 rpm, 20 min), and then, a 2 to 3-fold amount of extraction solvent may be added to the supernatant, and the resulting solution may be placed in a refrigerator (4° C.) and allowed to stand for 12 hours. The supernatant in the solution which had been allowed to stand may be obtained and centrifuged again (8,000 rpm, 20 min), and the precipitate may be recovered, thereby preparing a crude extracellular polysaccharide. The crude extracellular polysaccharide is preferably vacuum freeze dried at a temperature of 30° C. or lower.

The extraction solvent may be a solvent selected from the group consisting of water, ethanol, methanol, acetone, butanol and ethyl acetate, or a mixture thereof, and preferably, it may be water or 50% (w/w) to 80% (w/w) of aqueous solution of ethanol.

A composition for lowering blood pressure according to the present invention, comprising an extracellular polysaccharide produced by *Ceriporia lacerata*; a mycelial culture medium of *Ceriporia lacerata* containing the extracellular polysaccharide; or dried powders or an extract thereof, as an effective ingredient, may further contain a carrier, an excipient and a diluent which are commonly used.

The extracellular polysaccharide may be comprised in an amount of 0.1 to 80 wt %, preferably 0.1 to 50 wt %, based on the total weight of the composition, and a mycelial culture medium of *Ceriporia lacerata*, or dried powders or an extract thereof may be adequately comprised in an amount which corresponds to the above amount of the extracellular polysaccharide. However, the most preferred effective content of an extracellular polysaccharide, a mycelial culture medium containing the extracellular polysaccharide, or dried powders or an extract thereof may be adequately adjusted according to the method of use and purpose of the composition.

A composition according to the present invention can be formulated and used in accordance with a conventional method. Suitable formulations may include, but are not limited to, tablets, pills, powders, granules, sugar-coated tablets, hard or soft capsules, solutions, suspensions or emulsions, injections, suppositories, and the like.

A composition according to the present invention can be prepared into a suitable formulation using a pharmaceutically inert organic or inorganic carrier. That is, if the formulation is a tablet, a coated tablet, a sugar-coated tablet or a hard capsule, lactose, sucrose, starch or a derivative thereof, talc, calcium carbonate, gelatin, or stearic acid or a salt thereof may be used. Also, if the formulation is a soft capsule, vegetable oil, wax, fat, or semi-solid or liquid polyol may be used. Furthermore, if the formulation is in the form of a solution or syrup, water, polyol, glycerol, vegetable oil, and the like may be used.

A composition according to the present invention may further comprise a preservative, a stabilizer, a wetting agent, an emulsifier, a solubilizer, a sweetener, a coloring agent, an osmotic pressure regulator, an antioxidant, and the like in addition to the above carrier.

A method of administering a composition according to the present invention can be easily selected in accordance with the formulation, which may be oral or parenteral administration. The dosage may vary depending on the patient's age, lowering blood pressure, weight, disease severity, and/or route of administration, but is generally 5 to 500 mg/kg, preferably 100 to 250 mg/kg based on the extracellular polysaccharide, an effective ingredient, which may be administered in one to three divided doses a day. However, such dosage does not limit the scope of the present invention in any way.

A composition according to the present invention not only provides an excellent blood pressure-lowering effect but also shows little toxicity and adverse events, and thus can safely be used for the purpose of lowering blood pressure by long-term administration. Therefore, a composition of the present invention can be used for preventing and treating a disease requiring blood pressure-lowering such as, for example, hypertension, stroke, etc.

Furthermore, the present invention provides a health functional food having blood pressure-lowering effect, comprising an extracellular polysaccharide produced by *Ceriporia lacerata*; a mycelial culture medium of *Ceriporia lacerata* containing the extracellular polysaccharide; or dried powders or an extract thereof, as an effective ingredient.

A health functional food according to the present invention may be in the form of powders, granules, a tablet, a capsule or a drink, and may be a candy, a chocolate, a drink, a gum, a tea, a vitamin complex, a health supplementary food, and the like.

Herein, an extracellular polysaccharide, a mycelial culture medium containing the extracellular polysaccharide, or dried powders or an extract thereof according to the present invention may be generally comprised in a food in an amount of 0.01 to 50 wt %, preferably 0.1 to 20 wt % based on the total weight of the food, and may be generally comprised in a ratio of 0.02 to 10 g, preferably 0.3 to 1 g based on 100 mL of a health drink composition in the case of a health drink composition.

The food may further comprise a sitologically acceptable food supplementary additive in addition to an extracellular polysaccharide, a mycelial culture medium of *Ceriporia lacerata* containing the same, or dried powders or an extract thereof.

The present invention provides a method for lowering blood pressure comprising administering to a subject in need of lowering blood pressure an extracellular polysaccharide produced by *Ceriporia lacerata*; a mycelial culture medium of *Ceriporia lacerata* containing the extracellular polysaccharide; dried powders of the mycelial culture medium; or an extract of the mycelial culture medium.

The above subject may be a mammal, more specifically a human.

In addition, the present invention provides a use of an extracellular polysaccharide produced by *Ceriporia lacerata*; a mycelial culture medium of *Ceriporia lacerata* containing the extracellular polysaccharide; dried powders of the mycelial culture medium; or an extract of the mycelial culture medium for preparing a drug for lowering blood pressure.

The extracellular polysaccharide produced by *Ceriporia lacerata*; the mycelial culture medium of *Ceriporia lacerata* containing the extracellular polysaccharide; dried powders of the mycelial culture medium; or an extract of the mycelial culture medium are as described above.

In addition, the method for lowering blood pressure can be used for preventing or treating a disease requiring blood pressure-lowering such as, for example, hypertension, stroke, etc.

MODE FOR THE INVENTION

Hereinafter, the present invention will be described in more detail with the following Examples. The following Examples are provided to illustrate the present invention, but the scope of the present invention is not limited thereto.

EXAMPLES

1. Preparation of Culture Medium of *Ceriporia lacerata*, Dried Powders Thereof; Extract, and Extracellular Polysaccharide (Exopolysaccharide; Hereinafter Referred to as "EPS")

1.1 Preparation of Culture Medium of *Ceriporia lacerata*

*Ceriporia lacerata* isolated from *Quercus serrata* collected at Sangju city, Gyeongbuk province were subcultured to obtain a parent strain which was subsequently freeze-stored at −80° C., and the freeze-stored strain was cultured with 2-3 passages in PDA (Potato dextrose agar) medium (87 plastic bulbs; Difco, Becton Dickinson and Company), and the complete strains of sufficient amount alone were stored in a refrigerator at 4° C. until use. Then, 600 mL of the PDB (Potato dextrose broth) medium (Difco, Becton Dickinson and Company) was placed in an Erlenmeyer flask, and a PDA culture strain was added thereto and shake-cultured for 8 days.

And a liquid culture medium containing 1.5 wt % of sugar, 0.5 wt % of glucose, 0.5 wt % of potato starch, 0.25 wt % of sorghum powder, 0.25 wt % of barley powder, 0.75 wt % of soybean flour, 0.05 wt % of magnesium sulfate ($MgSO_4$), 0.05 wt % of monopotassium phosphate (KH$_2$PO$_4$), 0.05 wt % of dipotassium phosphate (K$_2$HPO$_4$) and residual quantity of water was sterilized for 20 minutes in a 800 L fermenter at 121° C. and 1.5 kgf/cm$^2$, and then, the medium was cooled to 23° C. and inoculated with 600 mL of the PDB culture strain to be as a starter. *Ceriporia lacerata* mycelia were liquid-cultured in the medium for 10 days at a constant temperature of 23° C., under a blue LED light source, with the air injected at 0.5 to 1.5 kgf/cm$^2$, and a carbon dioxide concentration of 2,000 ppm, to prepare the mycelial culture medium of *Ceriporia lacerata*.

1.2 Preparation of Dried Powders of Culture Medium of *Ceriporia lacerata*

The mycelial culture medium of *Ceriporia lacerata* prepared in the Preparation Example 1.1 was freeze-dried by a vacuum freeze dryer at the low temperature of 25° C. for 72 hours to form powders, to prepare the dried powders of mycelial culture medium of *Ceriporia lacerata*.

1.3 Preparation of Extract of Culture Medium of *Ceriporia lacerata*

5 g of the dried powders prepared in Preparation Example 1.2 was added to 100 mL of distilled water and sufficiently suspended, and then the resulting solution was centrifuged (at 8,000 rpm for 20 minutes). The supernatant separated therefrom was mixed with a 2- to 3-fold amount of ethanol and placed in a refrigerator (at 4° C.) and allowed to stand for 12 hours. The resultant supernatant was taken and an extract of the mycelial culture medium of *Ceriporia lacerata* was prepared therefrom.

1.4 Preparation of EPS from Culture Medium of *Ceriporia lacerata*

The extract prepared in Preparation Example 1.3 was further centrifuged (at 8,000 rpm for 20 minutes), and then the precipitate was recovered to obtain crude EPS. The crude EPS was dried in a freeze dryer for 72 hours to obtain a complete EPS.

Example 1. Evaluation of EPS Properties 1.1. Molecular Weight Measurement of EPS Using Gel Permeation Chromatography (GPC)

The EPS prepared in Preparation Example 1 was dissolved in a solution of 0.1 M Na$_2$SO$_4$/0.05 M NaN$_3$ (adjusted to pH 4 with glacial acetic acid) to a concentration of 1% (w/v), and then the mixture was centrifuged and the supernatant was isolated and filtered with a 0.45 μm syringe filter and analyzed by GPC.

The refractive index of the detector was used for the analysis; OHpak SB 805 HQ (Shodex, Japan) was used for the GPC column; and 0.1 M Na$_2$SO$_4$/0.05 M NaN$_3$ (adjusted to pH 4 with glacial acetic acid) was used for a mobile phase, which was allowed to flow at a flow rate of 1.0 mL/min. Standard curves were generated using dextrans (American Polymer Corporation, USA) with different molecular weights (130, 400, 770 or 1200 kDa), and the molecular weight of EPS was measured using refractive index (RI) measuring instrument Knauer K-2310 (Germany) (Table 1).

TABLE 1

|  | Measurement of molecular weight |
| --- | --- |
| HPLC system | Knauer K-501 system |
| Column | OHpak SB 805 HQ (Shodex, Japan) |
| Mobile phase | 0.1M Na$_2$SO$_4$/0.05M NaN$_3$/pH 4 |
| Flow rate | 1.0 mL/min |
| Measuring instrument | RI (Knauer K-2310) |

As a result, the molecular weight of EPS of the present invention was about 120 KDa.

1.2. Measurement of Sugar and Protein Contents of EPS

The EPS was subjected to secondary purification and treated with a protein-hydrolysis enzyme to measure sugar and protein contents.

Specifically, the primary-purified EPS was dissolved in distilled water again and centrifuged (at 8,000 rpm for 20 minutes) to separate the supernatant, and then a 2- to 3-fold amount of ethanol was added thereto. The mixture was placed in a refrigerator (at 4° C.) and allowed to stand for 12 hours. The resultant supernatant alone was centrifuged again (at 8,000 rpm for 20 minutes), and the precipitate was recovered to obtain a secondary-purified EPS. And the purified EPS was dissolved in distilled water and treated with Alcalase, a protein-hydrolysis enzyme, at a concentration of 0.5% (w/v) at 50° C. for 30 minutes.

The sugar content was measured by the phenol-sulfuric acid method. 25 μL of 80% phenol was added to 1 mL of each of the samples diluted at various concentrations, and then 2.5 mL of sulfuric acid was added thereto. The mixture was cooled to room temperature, and then the sugar content was calculated by measuring the absorbance at 465 nm.

The protein content was measured by BCA method (see Smith P K et al., *Analytical Biochemistry*, 150 (1): 76-85 (1985)) and bovine serum albumin was used as a standard.

As shown in Table 2 below, the sugar content was 45 to 51 wt % and the protein content was 33 to 34 wt %.

TABLE 2

|  | Yield (%) | Total sugar content (%) | Total protein content (%) |
| --- | --- | --- | --- |
| EPS | 1.22 ± 0.03 | 45.32 ± 1.41 | 34.17 ± 0.73 |
| Secondary-purified EPS | 0.78 ± 0.01 | 50.49 ± 0.52 | 33.50 ± 2.79 |
| Enzyme-treated EPS* | 0.24 ± 0.06 | 51.39 ± 1.32 | 34.61 ± 1.51 |

*Enzyme treatment: Alkalase 0.5%, 50° C., 30 minutes.
Each value represents mean ± SE (n ≥ 3).

Each value represents mean±SE (n≥3).

As a result of analyzing sugar content of EPS, it was found that EPS mainly contains mannose, galactose and glucose.

Example 2. Verification of Blood Pressure-Lowering Effect of EPS

In order to investigate the blood pressure-lowering effect of EPS isolated from the mycelial culture medium of *Ceriporia lacerata*, the EPS prepared in Preparation Example 1 was used at the concentrations of 1 μg/mL, 3 μg/mL, 10 μg/mL, and 30 μg/mL, and ACE inhibition activity of the EPS was measured with reference to the method described in a literature (Kwang-Sup Youn and Jae-Won Kim, *J. Korean Soc. Food Sci. Nutr.*, 41(10):1388-1394, 2012)

The ACE inhibition activities of captopril and EPS were compared and shown in FIG. 1.

As shown in FIG. 1, it was found that the ACE inhibition activity gradually increased as the concentration of EPS according to the present invention increased from 1 μg/mL to 30 μg/mL. In addition, the ACE inhibition activity was significantly superior to that of captopril, which is a known ACE inhibitor. This shows that the EPS according to the present invention has significant ACE inhibition activity at each concentration and has a significantly higher ACE inhibition activity than the positive control, captopril, and thus can be useful as a blood pressure-lowering agent.

The invention claimed is:

1. A method for lowering blood pressure comprising administering to a subject in need of lowering blood pressure a composition comprising an effective amount of at least one of (a)-(c):
   (a) a mycelial culture medium of *Ceriporia lacerate* containing an extracellular polysaccharide produced by the *Ceriporia lacerate*, wherein said extracellular polysaccharide is approximately 120 kDa as determined by gel permeation chromatography;
   (b) dried powders of the mycelial culture medium of *Ceriporia lacerate* of (a); and
   (c) a liquid extract of the dried powders of (b).

2. The method of claim 1, wherein the extracellular polysaccharide produced by *Ceriporia lacerate* contains mannose, galactose and glucose.

3. The method of claim 1, wherein the mycelial culture medium of *Ceriporia lacerate* containing an extracellular polysaccharide is prepared by a preparation method comprising a step of culturing mycelia of *Ceriporia lacerate* in a liquid to prepare the mycelial culture medium of *Ceriporia lacerate*.

4. The method of claim 3, wherein the liquid comprises sugar, glucose, starch, sorghum powder, barley powder, soybean flour, magnesium sulfate ($MgSO_4$), monopotassium phosphate ($KH_2PO_4$), dipotassium phosphate ($K_2HPO_4$) and water, and the hydrogen ion concentration of the medium is pH 4.5 to 6.0.

5. The method of claim 3, wherein the culturing in a liquid is conducted under a blue LED light source with a carbon dioxide concentration maintained at 1,000 to 2,000 ppm.

6. The method of claim 1, wherein the extracellular polysaccharide is comprised in an amount of 0.1 to 80 wt % based on the total weight of the composition.

7. The method of claim 1, wherein the composition is a pharmaceutical composition.

8. The method of claim 1, wherein the composition is a food in a form selected from the group consisting of a candy, a chocolate, a drink, a gum, a tea, a vitamin complex formulation, and a health supplementary food.

9. The method of claim 1, wherein the composition is a food in a form of powders, granules, a tablet, a capsule or a drink.

10. The method of claim 1, wherein the composition is a feed composition.

11. The method of claim 8, wherein the at least one of (a)-(c) is included in an amount of 0.01 to 50 wt % based on the total weight of the food.

12. The method of claim 9, wherein the at least one of (a)-(c) is included in an amount of 0.01 to 50 wt % based on the total weight of the food.

13. A method for inhibiting angiotensin converting enzyme in a subject in need thereof comprising administering to the subject a composition comprising an effective amount of at least one of (a)-(c):
   (a) a mycelial culture medium of *Ceriporia lacerate* containing an extracellular polysaccharide produced by the *Ceriporia lacerate*, wherein said extracellular polysaccharide is approximately 120 kDa as determined by gel permeation chromatography;
   (b) dried powders of the mycelial culture medium of *Ceriporia lacerate* of (a); and
   (c) a liquid extract of the dried powders of (b).

* * * * *